United States Patent [19]

Sielcken et al.

[11] Patent Number: 5,693,851
[45] Date of Patent: Dec. 2, 1997

[54] PROCESS FOR THE PREPARATION OF A MIXTURE OF ALKYL PENTENOATES

[75] Inventors: Otto E. Sielcken; Hans Hovenkamp, both of Sittard, Netherlands

[73] Assignees: DSM N.V., Netherlands; E. I. Du Pont de Nemours and Company, Wilmington, Del.

[21] Appl. No.: 596,406

[22] Filed: Feb. 2, 1996

Related U.S. Application Data

[63] Continuation of PCT/NL94/00191 Aug. 15, 1994.

[30] Foreign Application Priority Data

Aug. 23, 1993 [NL] Netherlands ................ 9300861

[51] Int. Cl.$^6$ ............................................. C07C 67/36
[52] U.S. Cl. ................................... 560/207; 560/206
[58] Field of Search .............................. 560/207, 206

[56] References Cited

U.S. PATENT DOCUMENTS

| | | |
|---|---|---|
| 4,748,261 | 5/1988 | Billig et al. . |
| 5,028,734 | 7/1991 | Drent . |
| 5,210,280 | 5/1993 | Drent . |

FOREIGN PATENT DOCUMENTS

| | | |
|---|---|---|
| 0 273 489 | 7/1988 | European Pat. Off. . |
| 0 284 170 | 9/1988 | European Pat. Off. . |
| 0 495 548 | 7/1992 | European Pat. Off. . |

OTHER PUBLICATIONS

Derwent Abstract re: JP-A-57126425, 1982.

Cullen et al., "Structure of the Hydrogenation Catalyst [(P$^\frown$P)Rh(NBD)]ClO$_4$, P$^\frown$P=($\eta^5$-[(CH$_3$)$_3$C]$_2$PC$_5$H$_4$)$_2$Fe, and Some Comparative Rate Studies", Organometallics (1983) 2, 714–719.

Knifton, "Syngas Reactions", Journal of Catalysis (1979) 60, 27–40.

*Primary Examiner*—Paul J. Killos
*Attorney, Agent, or Firm*—Cushman Darby & Cushman IP Group of Pillsbury Madison & Sutro LLP

[57] ABSTRACT

Process for the preparation of a mixture of alkyl pentenoates by carbonylation of butadiene in the liquid phase in the presence of an alkanol, carbon monoxide, palladium and a bidentate organic phosphorus, antimony or arsenic ligand, the bidentate ligand having as bridging group a bis($\eta$-cyclopentadienyl) coordination group of a transition metal. Preferably the transition metal is iron.

18 Claims, 1 Drawing Sheet

PROCESS FOR THE PREPARATION OF A MIXTURE OF ALKYL PENTENOATES

This is a continuation of International Application No. PCT/NL94/00191 filed Aug. 15, 1994 which designated the U.S.

The invention relates to a process for the preparation of alkyl pentenoates by carbonylation of butadiene in the liquid phase in the presence of an alkanol, carbon monoxide, palladium and a bidentate organic phosphorus, antimony or arsenic ligand.

Such a process is known from EP-B-273489. This patent specification describes the carbonylation of butadiene in the presence of an alkanol, carbon monoxide, a palladium compound and a bidentate organic phosporus ligand. The bridging group of the ligand, which connects the two phosphorus atoms, consisting of a bivalent organic compound having at least two carbon atoms. The examples of EP-B-273489 were performed with 1,4-di(diphenylphosphino) ethane, 1,4-di(diphenylphosphino)propane and 1,4-di (diphenylphosphino)butane.

A drawback of this known process is that the resulting mixture of isomeric alkyl 4-, 3- and 2-pentenoates contains a relatively large amount of alkyl 2-pentenoate: about 10-25% of all alkyl pentenoates formed is alkyl 2-pentenoate, at high butadiene conversion. This is disadvantageous if such a mixture would be used directly in the hydroformylation to the terminal alkyl 5-formyl-valerate with a rhodium-based catalyst system, such as for example described in U.S. Pat. No. 4,748,261. The alkyl 2-pentenoate in the mixture appears to have an adverse effect on the selectivity in the production of the alkyl 5-formylvalerate.

The object of the present invention is to provide a process for the carbonylation of butadiene wherein the formation of alkyl 2-pentenoate is suppressed.

This object is achieved in that the bidentate ligand has as bridging group a bis(η-cyclopentadienyl) coordination group of a transition metal.

It appears that when applying a bidentate phosphorus ligand as described above with such an organometallic bridging group (the divalent bis(n-cyclopentadienyl) coordination group is an organometallic group) the selectivity towards alkyl 2-pentenoate is in general lower than 6%, and in particular lower than 4% (relative to all isomeric alkyl pentenoates).

Furthermore the ligands according to the invention are considerably more stable in the presence of oxygen than the alkyl-substituted phosphorus ligands with an organic C2–C6 alkylene bridging group. This is advantageous because less measures have to be taken to handle the ligand oxygen free.

According to Derwent Abstract 82-77560E (JP-A-57126425) it is known to react a saturated organic halide to the corresponding ester with carbon monoxide and an alkanol in the presence of a carbonylation catalyst comprising a 1,1'-bis(diphenylarsino)ferrocene ligand and $PdCl_2$. The reaction, in which the halide group is reacted to an ester group, is however different from the present reaction in which an unsaturated compound is reacted to an ester.

The invention also relates to a process for the preparation of mainly alkyl 3-pentenoates. It has been found that the process according to the invention enables alkyl 3-pentenoates to be prepared with a high selectivity and yield. The alkyl pentenoate can be separated from the mixture of isomeric alkyl pentenoates by means of, for example, distillation.

The bidentate ligand may have the following general formula:

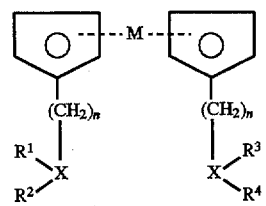

where n=0 or 1, X represents a phosphorus, antimony or arsenic atom, M represents a transition metal chosen from the group comprising Fe, Zr, Co, Cr, Ni, Ti, Ru and W, and the groups $R^1$, $R^2$, $R^3$ and $R^4$ represent an organic group with 1 to 20 carbon atoms. Examples of possible organic groups are aryl, alkyl, aralkyl, alkaryl groups and heterocyclic groups. Examples of possible aryl groups are phenyl and naphtyl groups. Examples of possible alkaryl groups are cumenyl, mesityl, tolyl and xylyl. Examples of heterocyclic groups are cyclic groups with nitrogen or sulphur atoms in the ring, for example pyridyl and thiophenyl.

Preferably at least one of the groups $R^1$–$R^4$ is an alkyl group preferably with 1 to 6 carbon atoms or an aralkyl group. With increasing preference two, three or all four of groups $R^1$–$R^4$ is an alkyl or an aralkyl group, because the corresponding bidentate ligands according to the invention are more stable under the carbonylation conditions of the proces of the invention. The most stable bidentate ligand has four alkyl or aralkyl groups. It further appears that the ligands in which $R^1$–$R^4$ are alkyl or aralkyl groups are more stable than the aryl substituted phosphorus ligands, like 1,4-di(phenylphosphino) butane described in EP-B-273489.

An examples of a possible aralkyl group is benzyl. Examples of possible alkyl groups are branched alkyl groups, for example isopropyl, isobutyl and tertbutyl and linear alkyl groups, for example, methyl, ethyl, propyl, butyl, pentyl and hexyl, and cyclic alkyl groups, for example, cyclohexyl and cyclooctyl.

The cycloalkyl group may optionally be substituted with $C_1$–$C_4$ alkyl groups, such as for instance methyl, ethyl, propyl, isopropyl, butyl, isobutyl or tertbutyl.

The organic groups $R^1$–$R^4$ may also be substituted with for instance $C_1$–$C_4$ alkoxy, amino and halogenide groups, for example chloride and bromide.

A preferred bidentate ligand has at least one phosphorus, antimony or arsenic atom which is bonded to two alkyl (branched or non-branched) or to two alkaryl groups or to one alkyl and one alkaryl group.

The cyclopentadienyl group of the metallocene compound may optionally be substituted with for instance one or more aryl or alkyl groups or with other functionalities. Examples of such groups are $C_1$–$C_4$ alkyl groups, such as methyl, ethyl, propyl, isopropyl, butyl, isobutyl, tert-butyl and carboxyl, hydroxyl, amino and halogenide groups for example chloride and bromide. Other possible substituents are divalent organic groups with 1–20 carbon atoms, which groups may be used to immobilize the bidentate ligand on a carrier. Examples of possible carriers are organic carriers for example polyethene, polystyrene, poly(styrene-co-diphenylbenzene) resin or inorganic carriers, for example silica, alumina and titanoxide.

Preferably, Fe is used as transition metal in the metallocene compound (the bridge group being a ferrocene). An example of a method how to prepare a ligand according to the invention is described in W. R. Cullen, F. W. B. Einstein, T. Jones, T.-J. Kim, Organometallics (1983), 2, 714.

Preferably, phosphorus ligands are used (with X in formula (1) is a phosphorus atom) because these ligands are more stable than the arsene or antimone based ligands.

Examples of suitable bidentate phosphine ligands according to the invention are 1,1'-bis(diphenylphosphino) ferrocene 1,1'-bis(isopropylphenylphosphino)ferrocene 1,1'-bis(diisopropylphosphino)ferrocene, 1,1'-bis(diisobutylphosphino)ferrocene, 1,1'-bis(dipropylphosphino)ferrocene, 1,1'-bis(dicyclohexylphosphino)ferrocene, 1,1'-bis(isopropylcyclohexylphosphino)ferrocene, 1,1'-bis(ditert.butylphosphino)ferrocene, 1-di(isopropylphosphino)-1'-(phenylisopropylphosphino)ferrocene. 1,1'-bis(di-2-thiophenylphosphino)ferrocene The alkanol as a rule is a hydrocarbon compound with 1 to 20 carbon atoms. The hydrocarbon compound may be an aliphatic, cycloaliphatic or aromatic (phenolic) compound and may be substituted with one or more inert groups. Examples of suitable aliphatic alkanols are methanol, ethanol, propanol, isopropanol, isobutanol, tert-butanol, butanol, pentanol and cyclohexanol. Examples of a suitable aromatic compound include cresol and phenol. Preferably, methanol and ethanol are used. The alkyl group of the alkyl pentenoate corresponds to the alkanol used.

The quantity of alkanol applied is not critical. The alkanol:butadiene molar ratio is as a rule between 0.1:1 and 10:1. Preferably the molar ratio of alkanol:butadiene is around 1:1.

All inert solvents are in principle suitable as additional solvent, but it is also possible to use an excess of one of the reactants or (by) products in such an amount that a suitable liquid phase is formed. A possible suitable reactant is the alkanol and examples of (by) products are the pentenoate, $C_9$-esters and high boiling by-products. Examples of inert solvents are sulphoxides and sulphones, such as for instance dimethyl sulphoxide, diisopropyl sulphone; aromatic solvents, such as benzene, toluene, xylene; esters, such as methyl acetate, methyl valerate, pentenoate esters and butyrolactone; ketones, such as acetone or methylisobutyl ketone; and ethers such as anisole, trioxanone, diphenyl ether and diisopropyl ether and mixtures of these solvents. Preferably, diphenyl ether is used as additional solvent.

The palladium: additional solvent molar ratio is as a rule between 1:20 and 1:300.

The palladium may be present in the reaction mixture as a heterogeneous palladium compound or as a homogeneous palladium compound. However, homogeneous systems are preferred. Since palladium in situ forms a complex with the bidentate ligand, the choice of the initial Pd compound is in general not critical. Examples of homogeneous palladium compounds are palladium salts of for instance nitric acid, sulphonic acid, alkane carboxylic acids with not more than 12 carbon atoms or hydrogen halogenides (F, Cl, Br, I), but metallic palladium may also be used. Examples of such palladium compounds are $PdCl_2$, $PdBr_2$, $PdI_2$, $Na_2PdI_4$, $K_2PdI_4$, $PdCl_2$ (benzonitrile)$_2$ and bis(allylpalladium chloride). Another group of suitable halogen-free palladium compounds are palladium complexes such as palladium acetylacetonate (Pd(acac)$_2$), Pd(II) acetate, Pd(NO$_3$)$_2$, o-toluyl phosphine palladium, and palladium (benzylidene acetone)$_2$. An example of a suitable heterogeneous palladium compound is palladium on an ion exchanger, such as for instance an ion exchanger containing sulphonic acid groups.

The bidentate ligand:palladium molar ratio is as a rule between 1:1 and 10:1. When this ratio is lower palladium can precipitate, whereas this ratio is higher, the catalytic effect is weaker and by-products such as vinyl cyclohexene and high-molecular products can form. It has been found that the optimum ratio will depend on the choice of the specific organic groups bounded to the phosphorus, arsenic or antimony atoms. Ligands with four alkyl or alkaryl groups, for example, have an optimum bidentate ligand:palladium ratio of between 1:1 and 1:2. Ligands with more aryl or aralkyl groups have as a rule a higher optimum ligand palladium ratio.

The molar quantity of palladium per molar quantity of butadiene is not critical and can for example be 500 times the quantity of butadiene. The butadiene:palladium molar ratio can as a rule be between 0.01:1 and 400:1. More palladium per mole of butadiene is not practical because large quantities of palladium are present during the reaction, while with less palladium per mole of butadiene the productivity will be less high, resulting in a large amount of by-products. Preferably, the butadiene:palladium molar ratio is between 1:1 and 300:1, most preferably the ratio is higher than 10:1 and lower than 200:1.

The process according to the invention is as a rule carried out at a temperature between 20° and 200° C. Preferably, the temperature is higher than 50° C. and lower than 160° C.

The (initial) pressure of carbon monoxide can as a rule be chosen from a wide range. Most preferably, the pressure is higher than 2.5 MPa and lower than 10 MPa.

The carbonylation is preferably carried out in the presence of a catalytically active quantity of a protonic acid with a pKa>3. It has been found that this leads to an increased alkyl pentenoate yield. The protonic acids are for example carboxylic acids with 1 to 30 carbon atoms. These carboxylic acids may be substituted with hydroxy $C_1$–$C_4$ alkoxy, amine and halogenide groups, for example chloride and bromide. Examples of preferred suitable carboxylic acids are benzoic acid or derived compounds, such as 2,4,6-trimethyl benzoic acid, meta- and parahydroxy benzoic acid. The amount of protonic acid with a pKa>3 is generally in the range of from 6 to 10 equivalents of acid per gram atom of palladium.

Another preferred acid with a pKa>3 is pentenoic acid because it can be easily obtained by saponifying the pentenoate formed in the process according to the invention. Another reason why the use of the pentenoic acid is advantageous is that if some of the acid reacts with the alkanol under the reaction conditions to the corresponding ester the desired alkyl pentenoate is obtained. Therefore the invention is also directed to a process for the preparation of alkyl pentenoates by carbonylation of butadiene according to the process of the invention as described above in the presence of pentenoic acid, in which pentenoic acid, consumed during carbonylation, is replaced with pentenoic acid obtained by saponification of an alkyl pentenoate. Preferably the alkyl pentenoate to be saponified is the same alkyl pentenoate obtained by the process according to the invention.

The invention is also directed to a process as described above in which as a source for palladium and the ligand a solid complex of palladium and this ligand is used. It has been found that when a complex of the ligand and palladium, preferably in a molar ratio of about 1:1, according to the invention are separately prepared before being added to the carbonylation reaction an improved activity of the catalyst and an improved selectivity to the desired alkyl 3-pentenoate is observed compared to the situation in which this complex is formed in situ. Such a complex of palladium and ligand, hereinafter called catalyst precursor, can be prepared by mixing a palladium compound as described above with the ligand according to the invention. This mixing is preferably performed in a solvent. Temperature and pressure are not critical. The temperature can be for example between 0° and 100° C. The pressure can be for example atmospheric pressure. The mixing is preferably performed in the absence of air. Examples of possible solvents are organic solvents, for example benzene, toluene, xylene or aliphatic solvents, for example hexane, methyl pentenoate, methanol, acetone, and ethanol. Preferably the complex is isolated from the mixture by crystallization of the complex under for example atmospheric pressure. The solid complex can be separated from the solvent by, for example by filtration or evaporation of the solvent. The solid catalyst precursor is air stable and can be easily supplied to the carbonylation reaction by for example disolving the catalyst precursor in one of the reactants or solvents and supplying the resulting mixture to the reaction.

The carbonylation according to the invention can optionally be carried out in the presence of a monodentate phosphine as also described in EP-A-273489.

The monodentate phosphine:bidentate ligand molar ratio is between 1:10 and 10:1.

The process according to the invention can be performed in the presence of organic nitrogen containing bases, in which the selectivity is not greatly influenced. The addition of these bases can be advantageous because they improve the catalyst stability as explained by Knifton in J. of Catalysis 60, (1979) page 29. Examples of aromatic nitrogen containing bases are N-heterocyclic bases, for example pyridine, alkylated pyridines, quinoline, lutidine, picolene, isoquinoline, alkylated quinolines and isoquinolines, acridine and N-methyl-2-pyrrolidone or N,N-dimethylaniline, N,N-diethylaniline, N,N-diethyltoluidine, N,N-dibutyltoluidine and N,N-dimethylformamide.

The amount (mol) of nitrogen containing base per mol palladium can for example be between 0 and 100 and more preferably between 1 and 30.

The reaction mixture may optionally contain one or more polymerization inhibitors. Suitable polymerization inhibitors can be quinones, nitro compounds, $Ph_2NH$ (Ph=phenyl), tert. butyl catechol and N.N'-naphthyl-p-phenylene diamine.

The invention is also directed to a continuous process for the preparation of alkyl pentenoates by carbonylation of butadiene according to the process of the invention as described above wherein the following steps are performed:
(a) carbon monoxide, alkanol, palladium and the bidentate ligand and optionally a protonic acid and a solvent are continuously brought into a reactor in which the carbonylation takes place,
(b) continuously separating part of the reaction mixture from the reactor,
(c) separating from the separated reaction mixture unreacted carbon monoxide, unreacted butadiene and unreacted alkanol and returning these reactants to step (a) and isolating the alkyl pentenoate and
(d) returning the remaining mixture of step (c), containing palladium and the bidentate ligand and optionally the solvent and the protonic acid, to step (a). Preferably a part of the remaining mixture of step (c) is separated from the mixture and led to a drain (purge) in order to prevent a build up of high boiling by-products in the circulating reaction mixture.

Step (a) can be performed in several ways. For example in a continously stirred tank reactor or a bubble column in which the product is simultaneously stripped from the liquid phase.

Separating the carbon monoxide, butadiene, alkanol and the alkyl pentenoate from the reaction mixture in step (c) can be performed in various ways. Generally the carbon monoxide is separated first from the reaction mixture in for example a simple gas-liquid separation unit. The butadiene, alkanol and the alkyl pentenoate can be seperated from the reaction mixture in one step followed by isolating the alkyl pentenoate from butadiene and alkanol. Preferably the butadiene and alkanol are separated from the reaction mixture in a separate step followed by the isolation of the alkyl pentenoate from the remaining reaction mixture. Separation of the various compounds can be performed in various ways, for example by simple flash operation or by distillation. The choice as to which unit operation is the most suitable will i.e. depend on the physical properties of the compounds to be separated.

The ratio of the remaining mixture of step (c) which is returned to step (a) and the part which is processed to a drain will depend on the amount of contaminations (for example high boiling by-products) allowed in the recirculating reaction mixture. When a large part will be sent to the drain a low degree of contamination in the recirculating reaction mixture will be the result and vice versa. The ratio of the remaining mixture of step (c) which is returned to step (a) and the part which is processed to a drain will depend on the amount of contamination formed in the process and the acceptable level of contamination in the circulating process stream.

The part which is sent to the drain will contain apart from the above mentioned contaminations also the valuable palladium and bidentate ligand and optionally acid and solvent (provided acid and solvent are used according to the invention). Preferably the palladium, bidentate ligand, acid and solvent will be isolated from this mixture in order to advantageously reuse these compounds in the carbonylation step (step (a)) according to the invention. Examples of possible processes to separate these valuable compounds from some of the by-products is by distillation, crystallization and extraction.

Figure 1:
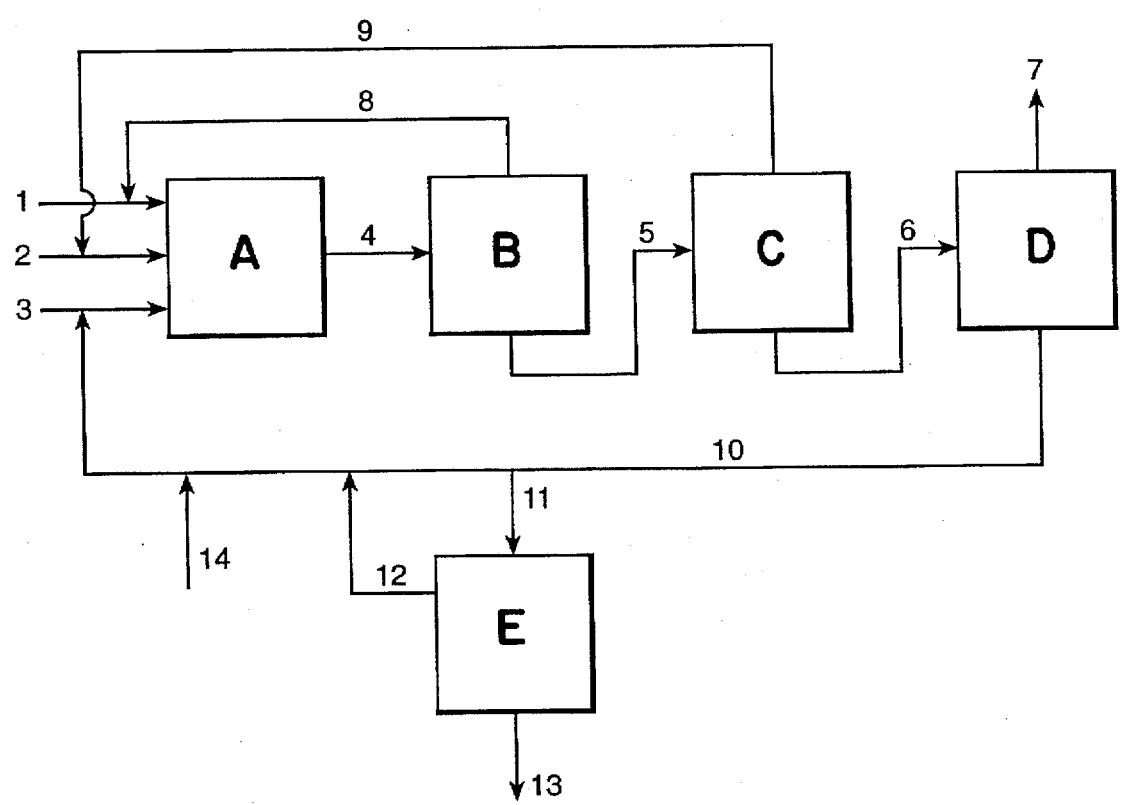
FIG. 1 illustrates a possible process scheme in which the process according to the invention can be performed.

Via (1) carbon monoxide, via (2) methanol and via (3) butadiene and optionally a solvent is continuously fed to the carbonylation reactor zone (A). In the reactor zone (A) the catalyst according to the invention is present. Via (4) the reactor effluent is led to a flash operation zone (B) in which carbon monoxide is separated from the effluent and returned to the reactor (A) via (8). The remaining mixture in (B) is led to a first distillation column (C) in which unreacted butadiene, possible intermediates and alkanol is separated from the mixture and returned to the reactor zone (A). The remaining mixture is led via (6) to distillation column (D) in which the pentenoate product is isolated (7) from the remaining mixture containing mostly catalyst, high boiling by-products and optionally a high boiling solvent. This remaining mixture is returned via (10) to the reactor zone (A). A part of stream (10) is led to a drain via (11). The catalyst and ligand present in (11) are separated from this mixture in (E) by for example crystallization and returned to the reactor zone via (12). A (almost) catalyst-free drain mixture is obtained (13). Fresh catalyst can be supplemented to the reactor zone via (14). The reactor zone can also be fed by any other combination of streams (1), (2), (3), (8), (9), (10) and (14) not shown in the figure.

When starting from a mixture of isomeric alkyl pentenoates (which contains alkyl 3-pentenoate and optionally some 4- and 2-pentenoate) prepared by the above described process according to the invention, it is possible to prepare alkyl 5-formylvalerate by hydroformylation in an high yield without first having to isolate 4- and/or 3-pentenoate from the alkyl 2-pentenoate.

Therefore this invention is also related to a process to prepare alkyl 5-formylvalerate by hydroformylation of a mixture of isomeric alkyl pentenoates obtained by the above described process in which the content of alkyl 2-pentenoate of this mixture is less than 4% (relative to all isomeric alkyl pentenoates). The hydroformylation process is in particular a rhodium catalyzed hydroformylation process and more in particular a homogeneously rhodium catalysed hydroformylation process, preferably also containing organic bidentate phosphorus containing ligands.

The invention will now be elucidated by means of the following non-restrictive examples.

The conversion and selectivity described in the examples and experiments are defined in the following manner:

$$\text{conversion} = \frac{\text{converted butadiene(*) (mol)}}{\text{initial amount of butadiene (mol)}} * 100\%$$

$$\frac{\text{selectivity of}}{\text{pentenoate}} = \frac{\text{obtained amount of pentenoate (mol)}}{\text{converted amount of butadiene(*) (mol)}} * 100\%$$

-continued (*)With converted butadiene is meant the amount of butadiene which is reacted to (by)products which cannot react in any way to the product 2-, 3- and 4-pentenoate. These (by)producgts are apart from the 2-, 3- and 4-pentenoates, for example butene, vinylcyclohexene and high boiling products for example $C_3$-heavies and higher boiling products. Excluded from this list are intermediates which can react to pentenoate.

EXAMPLE I

A 150 ml Parr autoclave, made of Hastelloy C, was filled successively with 0.168 g (0.75 mmol) of Pd(II)acetate, 0.605 g (1.45 mmol) of 1,1'-bis(diisopropylphosphino) ferrocene, 0.940 g (5.73 mmol) of 2,4,6-trimethyl benzoic acid, 3.300 g (103 mmol) of methanol and 38.2 g of diphenyl ether. The autoclave was closed and purged three times with 4.0 MPa carbon monoxide. Next, under a pressure of 1.0 MPa CO and with stirring at a speed of 1250 rpm, a mixture of 3.300 g (103 mmol) of methanol, 0.422 nonane (internal standard for GC product analysis), 0.573 g of cyclohexane (internal standard for butadiene analysis) and 3.48 g (64 mmol) of butadiene was injected under pressure from an injection vessel into the autoclave. The reaction mixture was brought to a temperature of 150° C. at a CO pressure of 6.5 MPa. After 4.5 hours the reaction was stopped and the butadiene and the reaction products were analyzed by gas' chromatographic methods.

The conversion was 80%. Selectivity: methyl 4-pentenoate=0.5%, methyl trans-3-pentenoate=67%, methyl cis-3-pentenoate=24%, methyl trans-2-pentenoate=2.5%, methyl cis-2-pentenoate=0%.

EXAMPLE II

Example I was repeated at 130° C.

After 5 hours of reaction the conversion was 90%. Selectivity: methyl 4-pentenoate=0%, methyl trans-3-pentenoate=70%, methyl cis-3-pentenoate=26%, methyl trans-2-pentenoate=1.9%, methyl cis-2-pentenoate=0%.

Comparative Experiment A

Example II was repeated with a ligand of EP-B-273489: 1,4-bis(diphenylphosphino)butane instead of 1,1'-bis(diisopropylphosphino)ferrocene. The ligand:palladium ratio was 4 (1.7 g (0.75 mmol) of Pd(II)acetate).

After 6 hours of reaction the conversion was 87%. Selectivity: methyl 4-pentenoate=0%, methyl trans-3-pentenoate=63%, methyl cis-3-pentenoate=23%, methyl trans-2-pentenoate=11%, methyl cis-2-pentenoate=0.1%.

The results of Examples I–II and Comparative Experiment A are summarized in Table 1.

TABLE 1

| no. | temp (°C.) | time (h) | L/Pd 1) | Conv. (%) | 4-MP 2) (%) | t-3-MP (%) | c-3-MP (%) | t-2-MP (%) | c-2-MP (%) |
|---|---|---|---|---|---|---|---|---|---|
| I | 150 | 4,5 | 1,9 | 80 | 0,5 | 67 | 24 | 2,5 | 0 |
| II | 130 | 5 | 1,9 | 90 | 0 | 70 | 26 | 1,9 | 0 |
| A | 130 | 6 | 4 | 87 | 0 | 63 | 23 | 11 | 0,1 |

1) L/Pd is the ligand:Pd ratio (mol/mol)
2) 4-MP is the selectivity of the methyl 4-pentenoate in %; t-3-MP is methyl trans-3-pentenoate; c means cis.

EXAMPLE III

Example II was repeated with the palladium replaced by bis(dibenzylidene acetone)palladium (0.75 mmol).

After 5 hours of reaction a conversion of 65% was reached. The selectivity towards the different products was as follows:
methyl 4-pentenoate=0.2%,
methyl trans-3-pentenoate=59%,
methyl cis-3-pentenoate=25%,
methyl trans-2-pentenoate=1.6%,
methyl cis-2-pentenoate=0.0%.

EXAMPLE IV

Example II was repeated with diphenyl ether replaced by the same volume of methyl valerate. After 5 hours of reaction a conversion of 88% was reached. The selectivity towards the different products was as follows:
methyl 4-pentenoate=0.0%,
methyl trans-3-pentenoate=68.0%,
methyl cis-3-pentenoate=25.1%,
methyl trans-2-pentenoate=3.5%,
methyl cis-2-pentenoate=0.1%.

In Comparative Experiments D and E it will be shown that formyl valerate ester is prepared with a higher selectivity when the alkyl 3-pentenoate is started from instead of the alkyl 2-pentenoate by hydroformylation using the process as described in U.S. Pat. No. 4,748,261.

Comparative Experiment D

A 150 ml Parr autoclave, made of Hastelloy C steel, was filled, under nitrogen, with 3.87 mg (0.0155 mmol) of Rh(acac)(CO)2, 40 ml of toluene and 0.375 mmol of a bidentatephosphite ligand (ligand/rhodium=25), the bidentate phosphite ligand having the following structure:

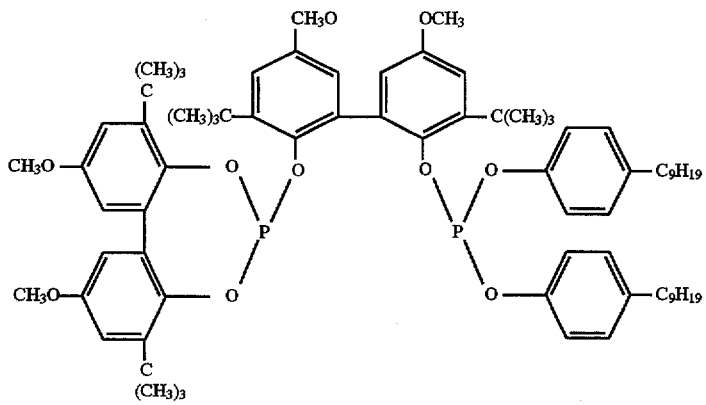

(II)

The autoclave was then closed, purged with nitrogen and heated to 90° C. at a pressure of 10 MPa carbon monoxide/hydrogen (1:1). Next, a mixture of 1.0 g of nonane (internal standard) and 3.40 g (29.8 mmol) of methyl 3-pentenoate (80% trans- and 20% cis-) made up to 10 ml with toluene was injected into the autoclave.

After 25 hours of reaction a conversion of 69% was reached. The selectivity towards methyl 5-formyl valerate was 81%. The overall selectivity towards aldehydes was 97% (linear/branched aldehydes=5). The selectivity towards the by-product methyl valerate was 3%.

Comparative Experiment E

Comparative Experiment D was repeated with methyl trans-2-pentenoate.

After 70 hours of reaction a conversion of 52% was reached. The selectivity towards methyl 5-formyl valerate was 27%. The overall selectivity towards aldehydes was 34%. A selectivity of 66% towards the by-product methyl valerate was found.

Comparison of Experiment D and E illustrates the negative influence of alkyl 2-pentenoates when preparing alkyl 5-formylvalerate by hydroformylating a mixture of isomeric alkyl pentenoates.

EXAMPLE V

A 150 ml Parr autoclave made of Hastelloy C steel was charged with 0.25 g Pd(II)acetate (1.1 mmol), 0.46 g 1,1'-bis(diisopropylphosphino)ferrocene (1.1 mmol), and 1.34 g (8.2 mmol) 2,4,6-trimethylbenzoic acid. The autoclave was closed. After having flushed with nitrogen 25 g diphenylether (deaerated and nitrogen flushed) was brought into the autoclave. The autoclave was flushed with carbon monoxide by pressurizing to 3.0 MPa and depressurizing and the mixture was stirred for 2 hours at room temperature and 0.1 MPa CO. After having set the pressure at 3.0 MPa CO and the temperature at 60° C. a mixture of 10.03 g 1,3-butadiene (204 mmol), 6.98 g methanol (218 mmol), 0.6231 g nonane (internal standard GC-analyses for pentenoates), and 0.422 g cyclohexane (internal standard butadiene analyses) was injected. The temperature was raised to 140° C. and 8.0 MPa CO. During the reaction the pressure was kept in the range of 4–8 MPa CO. The starting pressure was 8 MPa. When during the reaction the pressure dropped to 4 MPa the pressure was again raised to 8 MPa. After 2.5 hours no more CO was fed to the reactor and the reactor was cooled to room temperature. The reaction mixture was analyzed by GC methods for butadiene and reaction products. The conversion was 76%. Selectivity:methyl 4-pentenoate=0%; trans methyl 3-pentenoate=59%; cis methyl 3-pentenoate=26%; trans methyl 2-pentenoate=0.9%; cis methyl 2-pentenoate=0%.

EXAMPLE VI

A catalyst precursor was prepared by dissolving, under an atmosphere of nitrogen, 0.25 g Pd(II)acetate (1.1 mmol) and 0.50 g 1,1'-bis(diisopropylphosphino)ferrocene (1.2 mmol) in 10 ml deaerated and nitrogen purged toluene. After stirring overnight at room temperature the resulting orange mixture was slowly added during 5 minutes into 120 ml hexane (deaerated and nitrogen purged). The obtained precipitate was collected by filtration (under nitrogen) and dried in vacuum yielding 0.71 g of an orange solid.

EXAMPLE VII

The catalyst precursor of Example VI (0,7 g; 1.1 mmol precursor (based on Pd)) was dissolved, under an atmosphere of nitrogen, in 27 g diphenyl ether (deaerated and nitrogen flushed). The solution was introduced into the nitrogen flushed autoclave that contained 1.52 g 2,4,6-trimethylbenzoic acid. At 60° C. and 3.0 MPa CO a mixture of 9.60 g 1,3-butadiene (177 mmol), 5.76 g methanol (180 mmol), 0.4437 g nonane (internal standard GC-analyses for pentenoates), and 0.342 g cyclohexane (internal standard butadiene analyses) was injected. The temperature was raised to 140° C. and 8.0 MPa CO. During the reaction the pressure was kept in the range 4–8 MPa CO as in Example V. After 2.5 hours no more CO was fed to the reactor and the reactor was cooled to room temperature. The reaction mixture was analyzed by GC methods for butadiene and reaction products. The conversion was 95%. Selectivity:methyl 4-pentenoate=0.2%; trans methyl 3-pentenoate=64%; cis methyl 3-pentenoate=28%; trans methyl 2-pentenoate=2.0%; cis methyl 2-pentenoate=0%.

Comparison between Example V and VII illustrates the improvement in conversion achieved when applying a catalyst precursor as prepared in Example VI.

EXAMPLE VIII

The catalyst precursor of Example VI (0.7 g) was dissolved, under an atmosphere of nitrogen, in 25 g diphenyl ether (deaerated and nitrogen flushed). To this solution 0.2 mmol extra 1,1'-bis(diisopropylphosphino-ferrocene was added. The solution was introduced into the nitrogen flushed autoclave (same autoclave as in Example V) that contained 1.59 g 2,4,6-trimethylbenzoic acid. At 60C and 3.0 MPa CO pressure a mixture of 9.36 g 1,3-butadiene (173 mmol), 5.28 g methanol (165 mmol), 0.637 g nonane, and 0.419 g cyclohexane was injected. The temperature was raised to 140° C. and 8 MPa CO. During the reaction the pressure was kept in the range 4–8 MPa CO as in Example V. After 2.5 hours the reactor was cooled to room temperature. The reaction mixture was analyzed by GC methods for butadiene and reaction products. The conversion was 80%. Selectivity: methyl 4-pentenoate=0.1%; trans methyl 3-pentenoate=64%; cis methyl 3-pentenoate=29%; trans methyl 2-pentenoate=1.9%; cis methyl 2-pentenoate=0%.

The reaction mixture was transferred, under an atmosphere of nitrogen, from the autoclave into a batch vacuum distillation apparatus and distilled at 80° C. and 0.2 mm Hg. First carbon monoxide was separated from the mixture. Unreacted butadiene intermediates and methanol were separated and at least 99.6% of the pentenoate was isolated. The residue was returned into the autoclave. In a similar way as described above a second run was performed by injection of 169 mmol butadiene, 160 mmol methanol, 0.516 g nonane, and 0.460 cyclohexane. After 2.5 hours the reactor was cooled to room temperature. The conversion was 76%. Selectivity: methyl 4-pentenoate=0.1%; trans methyl 3-pentenoate=66%; cis methyl 3-pentenoate=29%; trans methyl 2-pentenoate=1.4%; cis methyl 2-pentenoate=0%.

This Example illustrates that the catalyst can be easily separated from the rest of the reaction mixture and that the catalyst can be reused in the carbonylation reaction according to the invention. Comparison of the conversion of Example VII and VIII shows an optimum bidentate ligand-palladium ratio.

EXAMPLE IX

A 50 ml Parr autoclave made of Hastelloy C steel was charged with 0.12 g Pd(II)acetate (0.53 mmol), 0.31 g 1,1'-bis(di-2-thiophenylphosphino)ferrocene (0.53 mmol), and 0.60 g (3.66 mmol) 2,4,6-trimethylbenzoic acid. The autoclave was closed. After having flushed with nitrogen 16 g diphenylether (deaerated and nitrogen flushed) was brought into the autoclave. The autoclave was flushed with carbon monoxide by pressurizing to 3 MPa and subsequently depressurizing. After having set the CO pressure at 3 MPa and the temperature at 60° C. a mixture of 2.07 g 1,3-butadiene (38 mmol), 3.71 g methanol (116 mmol), 0.307 g nonane (internal standard GC-analyses for pentenoates), and 0.343 g cyclohexane (internal standard butadiene analyses) was injected. The temperature was raised to 130° C. and 6.5 MPa CO. During the reaction the pressure was kept in the range 5.5–6.5 MPa CO as in Example V. After 3 hours the reactor was cooled to room temperature. The reaction mixture was analyzed by GC methods for butadiene and reaction products. The conversion was 58%. Selectivity: methyl 4-pentenoate=0.4%; trans methyl 3-pentenoate=67%; cis methyl 3-pentenoate=27%; trans methyl 2-pentenoate=1.2%; cis methyl 2-pentenoate=0%.

EXAMPLE X

A catalyst precursor was prepared as described in example VI from 0.25 g Pd(II)acetate (1.1 mmol) and 0.58 g 1,1'-bis(isopropylphenylphosphino)ferrocene (1.2 mmol). The solid catalyst precursor was dissolved, under an atmosphere of nitrogen, in 24 g diphenyl ether (deaerated and nitrogen flushed). The solution was introduced into a nitrogen flushed 150 ml Parr autoclave made of Hastelloy C steel that contained 1.76 g 2,4,6-trimethylbenzoic acid. At 60° C. and 3 MPa CO a mixture of 8.43 g 1,3-butadiene (156 mmol), 5.20 g methanol (163 mmol), 0.3391 g nonane (internal standard GC-analyses for pentenoates), and 0.314 g cyclohexane (internal standard butadiene analyses) was injected. The temperature was raised to 140° C. and 8 MPa CO. During the reaction the pressure was kept in the range 5–7 MPa CO as in Example V. After 2.5 hours the reactor was cooled to room temperature. The reaction mixture was analyzed by GC methods for butadiene and reaction products. The conversion was 91%. Selectivity: methyl 4-pentenoate=0.1%; trans methyl 3-pentenoate=66%; cis methyl 3-pentenoate=26%; trans methyl 2-pentenoate=2.3%; cis methyl 2-pentenoate=0%.

EXAMPLE XI

A catalyst precursor was prepared as described in example VI from 0.127 g Pd(II)acetate (0.56 mmol) and 0.257 g 1,1'-bis(diphenylphosphino)ferrocene (0.56 mmol). The solid catalyst precursor was dissolved, under an atmosphere of nitrogen, in 11 g diphenyl ether (deaerated and nitrogen flushed). The solution was introduced into a nitrogen flushed 50 ml Parr autoclave made of Hastelloy C steel that contained 0.86 g 2,4,6-trimethylbenzoic acid. At 60° C. and 3 MPa CO pressure a mixture of 5.09 g 1,3-butadiene (94 mmol), 4.51 g methanol (141 mmol), 0.961 g nonane (internal standard GC-analyses for pentenoates), and 0.512 g cyclohexane (internal standard butadiene analyses) was injected. The temperature was raised to 140° C. and 8 MPa CO. During the reaction the pressure was kept in the range 5–7 MPa CO as in Example V. After 2.5 hours the reactor was cooled to room temperature. The reaction mixture was analyzed by GC methods for butadiene and reaction products. The conversion was 44%. Selectivity: methyl 4-pentenoate=0%; trans methyl 3-pentenoate=61%; cis methyl 3-pentenoate=26%; trans methyl 2-pentenoate=0.9%; cis methyl 2-pentenoate=0%.

EXAMPLE XII

A catalyst precursor was prepared as described in example VI from 0.124 g Pd(II)acetate (0.55 mmol) and 0.284 g 1,1'-bis(dicyclohexylphosphino)ferrocene (0.60 mmol). The solid catalyst precursor was dissolved, under an atmosphere of nitrogen, in 10 g diphenyl ether (deaerated and nitrogen flushed). The solution was introduced into a nitrogen flushed 50 ml Parr autoclave, made of Hastelloy C steel, that contained 0.80 g 2,4,6-trimethylbenzoic acid. At 60° C. and 3 MPa CO pressure a mixture of 6.29 g 1,3-butadiene (117 mmol), 3.75 g methanol (117 mmol), 0.723 g nonane (internal standard GC-analyses for pentenoates), and 0.362 g cyclohexane (internal standard butadiene analyses) was injected. The temperature was raised to 140° C. and 8 MPa CO. During the reaction the pressure was kept in the range 5–7 MPa CO as in Example V. After 2.5 hours the reactor was cooled to room temperature. The reaction mixture was analyzed by GC methods for butadiene and reaction products. The conversion was 82%. Selectivity: methyl 4-pentenoate=0.1%; trans methyl 3-pentenoate=64%; cis methyl 3-pentenoate=28%; trans methyl 2-pentenoate=1.1%; cis methyl 2-pentenoate=0%.

EXAMPLE XIII

A catalyst precursor was prepared as described in example VI from 0.26 g Pd(II)acetate (1.1 mmol) and 0.51 g 1,1'- bis(diisopropylphosphino)ferrocene (1.2 mmol). The solid catalyst precursor was dissolved, under an atmosphere of nitrogen, in 24 g diphenyl ether (deaerated and nitrogen flushed). The solution was introduced into a nitrogen flushed 150 ml Parr autoclave that contained 1.59 g 2,4,6-trimethylbenzoic acid and 1.08 g pyridine (14 mmol). At 60° C. and 3 MPa CO a mixture of 11.2 g 1,3-butadiene (207 mmol), 6.72 g methanol (210 mmol), 0.460 g nonane (internal standard GC-analyses for pentenoates), and 0.561 g cyclohexane (internal standard butadiene analyses) was injected. The temperature was raised to 140° C. and 8 MPa CO. During the reaction the pressure was kept in the range 5–7 MPa CO. After 2.5 hours the reactor was cooled to room temperature. The reaction mixture was analyzed by GC methods for butadiene and reaction products. The conversion was 87%. Selectivity: methyl 4-pentenoate=0.1%; trans methyl 3-pentenoate=61%; cis methyl 3-pentenoate=30%; trans methyl 2-pentenoate=1.9%; cis methyl 2-pentenoate=0%.

We claim:

1. A process for the preparation of alkyl pentenoates by carbonylation of butadiene in the liquid phase in the presence of an alkanol, carbon monoxide, palladium and a bidentate organic phosphorous, antimony or arsenic ligand, wherein the bidentate ligand has, as a bridging group, a bis(η-cyclopentadionyl) coordination group of a transition metal.

2. A process according to claim 1, wherein the bidentate ligand has the following general formula:

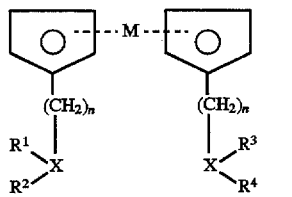
(I)

wherein n=0 or 1, X represents a phosphorous, antimony or arsenic atom, the groups $R^1$, $R^2$, $R^3$ and $R^4$ represent an organic group with 1–20 carbon atoms and M represents the transition metal.

3. A process according to claim 1 or 2, wherein the transition metal is selected from the group consisting of Fe, Zr, Co, Ru, Cr, Ni, Ti and W.

4. A process according to claim 3, wherein M is Fe.

5. A process according to claim 1 or 2, wherein at least one of the $R^1$, $R^2$, $R^3$ and $R^4$ groups is an alkyl or an aralkyl group with 6 to 10 carbon atoms.

6. A process according to claim 5, wherein at least one of the phosphorous, antimony or arsenic atoms is bonded to two alkyl or two aralkyl groups or to one alkyl and one aralkyl group.

7. A process according to claim 1 or 2, wherein the bidentate ligand is a bidentate phosphine ligand.

8. A process according to claim 1 or 2, wherein the bidentate ligand to palladium molar ratio is between 1:1 and 10:1.

9. A process according to claim 1 or 2, wherein the bidentate ligand to palladium molar ratio is between 1:1 and 2:1.

10. A process according to claim 1 or 2, wherein the butadiene to palladium molar ratio is between 1:1 and 200:1.

11. A process according to claim 10, wherein the butadiene to palladium molar ratio is between 10:1 and 200:1.

12. A process according to claim 1 or 2, wherein a catalytically active quantity of a protonic acid with a $pKa \geq 3$ is present.

13. A process according to claim 1 or 2, wherein the alkanol to butadiene molar ratio is between 0.1:1 and 10:1.

14. A process for preparation of alkyl pentenoates by carbonylation of butadiene in the liquid phase under effective carbonylation conditions in the presence of an alkanol, carbon monoxide, protonic acid having a $pKa \geq 3$, palladium and a bidentate phosphine ligand having a ferrocene bridging group.

15. A continuous process for the preparation of alkyl pentenoates by carbonylation of butadiene, in which continuous process the following steps are performed:

(a) continuously alkanol, carbon monoxide and butadiene are fed to a reactor zone in which the preparation of the alkyl pentenoate takes place according to claims 1 or 2;

(b) continuously separating part of the reaction mixture from the reactor zone;

(c) separating from the separated reaction mixture from (b) unreacted carbon monoxide, unreacted butadiene and unreacted alkanol and returning these reactants to step (a), and isolating the alkyl pentenoate; and (d) returning the remaining mixture of step (c), containing palladium and the bidentate ligand and optionally the solvent and the protonic acid, to step (a).

16. A process according to claim 15, wherein a part of the remaining mixture of step (c) is separated from the mixture and led to a drain in order to prevent a build up of high boiling by-products in the circulating reaction mixture.

17. A process for the preparation of alkyl 3-pentenoate which comprises separating the alkyl 3-pentenoate from a mixture of alkyl pentenoates which is obtained by a process according to claim 1 or 2.

18. A process for the preparation of alkyl 5-formyl valerate which comprises hydroformylating a mixture of isomeric alkyl pentenoates obtained by a process according to any one of claim 1 or 2, wherein said mixture contains less than 4%, relative to all isomeric alkyl pentenoates, of alkyl 2-pentenoates.

* * * * *